United States Patent
Dement et al.

(10) Patent No.: US 6,432,956 B1
(45) Date of Patent: Aug. 13, 2002

(54) METHOD FOR TREATMENT OF SLEEP APNEAS

(76) Inventors: William C. Dement, 440 Gerona Rd., Stanford, CA (US) 94305; Mark R. Rosekind, 1761 Lantis La., Los Altos, CA (US) 94022; Jeffrey L. Schwimmer, 31 Egbert Ave., Morristown, NJ (US) 07960

( * ) Notice: Subject to any disclaimer, the term of this patent is extended or adjusted under 35 U.S.C. 154(b) by 0 days.

(21) Appl. No.: 07/695,325

(22) Filed: May 3, 1991

Related U.S. Application Data

(63) Continuation-in-part of application No. 07/657,332, filed on Feb. 12, 1991, now abandoned, which is a continuation-in-part of application No. 07/479,803, filed on Feb. 12, 1990, now abandoned, which is a continuation of application No. 07/478,820, filed on Feb. 12, 1990, now abandoned.

(51) Int. Cl.$^7$ ........................ A61K 31/495; A61K 31/50
(52) U.S. Cl. ..................... 514/252.1; 514/252.12; 514/252.14; 514/252.18; 514/253.01; 514/253.12; 514/253.13
(58) Field of Search ................. 514/252, 278, 514/923, 252.1, 252.12, 252.14, 252.18, 253.01, 253.12, 253.13

(56) References Cited

U.S. PATENT DOCUMENTS

| | | | |
|---|---|---|---|
| 3,717,634 A | 2/1973 | Wu et al. | 544/230 |
| 3,976,776 A | 8/1976 | Wu et al. | 514/252 |
| 4,002,751 A * | 1/1977 | Linder | 424/250 |
| 4,182,763 A | 1/1980 | Casten et al. | 514/252 |
| 4,264,599 A * | 4/1981 | Eichenberger et al. | 424/250 |
| 4,335,138 A * | 6/1982 | Wiendorff et al. | 424/275 |
| 4,438,119 A | 3/1984 | Allen et al. | 514/252 |
| 4,567,185 A * | 1/1986 | Sackner | 514/282 |
| 4,634,703 A | 1/1987 | Kurtz et al. | 514/252 |
| 4,640,921 A | 2/1987 | Othmer et al. | 514/252 |
| 4,687,772 A | 8/1987 | Alderdice | 514/273 |
| 4,777,173 A | 10/1988 | Shrotryia et al. | 514/252 |
| 4,822,797 A * | 4/1989 | Okushima et al. | 514/255 |

OTHER PUBLICATIONS

Rapoport, et al, *Fed. Am. Soc. Exp. Bowl*, J.2:5, abstract 7030.*
Y.H. Wu et al, *J. Med. Chem.*, 15,477 (1972).
L.E. Allen et al, Arzneium. Forsch., 24, No. 6, 917–922 (1974).
G.L. Sathananthan et al, *Current Therapeutic Research*, 18/5, 701–705 (1975).
Gamer et al, *Am. Rev. Respir. Dis.*, 137:4, pp. 946–950 (1989).
Rapoport et al, *Fed. Am. Soc. Exp. Biol.* J 2:5, Abstract 7030 (1988).

* cited by examiner

*Primary Examiner*—Theodore J. Criares
(74) *Attorney, Agent, or Firm*—Richard P. Ryan

(57) ABSTRACT

Certain azapirone compounds and their pharmaceutically acceptable salts are useful in the treatment of sleep apneas.

13 Claims, No Drawings

METHOD FOR TREATMENT OF SLEEP APNEAS

CROSS REFERENCES TO RELATED APPLICATIONS

This application is a continuation-in-part of application Ser. No. 07/479,803, filed Feb. 12, 1990, now abandoned and application Ser. No. 07/657,332, filed Feb. 12, 1991, now abandoned which is a continuation of application Ser. No. 07/478,820, filed Feb. 12, 1990, now abandoned.

BACKGROUND OF THE INVENTION

This invention is concerned with a drug bioaffecting body-treating process that employs members of the general "azapirone" structural class of psychotropic agents. The archetypical compound of the azapirone class of agents has the following structural formula

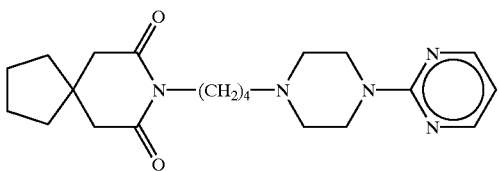

and is known as buspirone. The hydrochloride salt has been referred to in the prior art as MJ 9022-1 and as buspirone hydrochloride. Other acid addition salts thereof are named by combining "buspirone" with the appropriate word to define the acid from which it is prepared as in "buspirone hydrochloride". The latter is the United States Adopted Name (USAN); refer to J. American Med. Assoc. 225, 520 (1973).

The synthesis of the compound and the disclosure of its psychotropic properties are described in the following patents and publications.

1. Y. H. Wu, et al., *J. Med. Chem.*, 15,477 (1972).
2. Y.H. Wu, et al., U.S. Pat. No. 3,717,634 which issued Feb. 20, 1973.
3. L. E. Allen et al., Arzneium. Forsch., 24, No. 6, 917–922 (1974).
4. G.L. Sathananthan, et al., *Current Therapeutic Research,* 18/5, 701–705 (1975).
5. Y. H. Wu, et al., U.S. Pat. No. 3,976,776, issued Aug. 24, 1976.

The following patent references disclose and claim additional uses that relate to buspirone's pharmacological effects on the central nervous system.

6. The use of buspirone hydrochloride as a novel antianxiety agent for the treatment of neurotic patients is described in G. P. Casten, et al., U.S. Pat. No. 4,182,763, issued Jan. 9, 1980.
7. Allen, et al., disclose the use of buspirone in treating extrapyramidal motor disorders in U.S. Pat. No. 4,438, 119, issued Mar. 20, 1984.
8. Buspirone's use in sexual dysfunction was described by Othmer, et al., in U.S. Pat. No. 4,640,921, issued Feb. 3, 1987.
9. Kurtz, et al., in U.S. Pat. No. 4,634,703, issued Jan. 6, 1987 disclose buspirone's use in treating panic disorders.
10. Alderdice discloses the use of buspirone in the improvement of short term memory in U.S. Pat. No. 4,687,772, issued Aug. 18, 1987.
11. U.S. Pat. No. 4,777,173, issued Oct. 10, 1988 to Shrotriya and Casten, discloses and claims the use of buspirone in treating alcohol abuse.

Buspirone and related members of the azapirone class of psychotropic agents share common pharmacological actions, due perhaps to similar interactions of these compounds with monoaminergic pathways in particular areas of the brain. Specifically, functional binding of these agents at monoaminergic receptor sites in the brain indicate a more or less common neuropharmacologic profile for azapirones that would render members of the class useful equivalents when applied to pharmacological applications involving neural mechanisms.

The present invention resulted from the unexpected discovery that the representative azapirone, buspirone, was effective in treating patients suffering from sleep apneas. The only literature relating to the effects of any of the azapirones on respiration in general, concerned disclosures that buspirone had a stimulatory effect on respiration both in cats (Garner, et al., *Am. Rev. Respir. Dis.*, 137:4, pages 946–950 (1989)) and in normal male volunteers (Rapoport, et al., *Fed. Am. Soc. Exp. Biol.*, J 2:5, Abstract 7030 (1988).

It has become apparent that sleep apneas comprise a spectrum of related disorders with varying severity and morbidity. Sleep apneas have been usually classified as being an obstructive, central, or mixed apnea, depending on the presence or absence of respiratory efforts during the periods in which airflow has ceased. Obstructive and mixed apneas occur with greatest frequency with the most familiar being obstructive sleep apnea syndrome in which sporadic recurring collapse of the patient's upper airway occurs during sleep. If the collapse is complete there is no air exchange at the nose and mouth and breathing is interrupted. The usual result is a partial arousal from sleep and a return to normal breathing. The patient in most instances has no knowledge or memory of these apnea episodes but finds himself constantly suffering from fatigue and daytime sleepiness for no apparent reason. These recurrent apnea episodes with resultant hypoxemia and fragmented sleep can have serious neurologic and cardiac consequences. In recent years there has been a growing awareness of the seriousness of the sleep apnea problem due to its wide occurrence and the lack of a recognized effective treatment.

Surgical and mechanical interventions as well as oxygen administration have been employed as treatments. None of these are very suitable. Treatment of sleep apneas by pharmacological intervention has also had little success. Respiratory stimulants, theophylline, antidepressants and progestational agents have been used to treat sleep apneas but have not been found to be very effective.

In sum, there is nothing in the prior art, including the specific references set forth hereinabove, that would suggest the use of buspirone or other azapirones for the treatment of sleep apneas.

SUMMARY OF THE INVENTION

The method of the present invention is intended for the treatment of patients suffering from sleep apneas. The method essentially involves administration of an azapirone; buspirone is preferred, or a pharmacologically acceptable acid addition salt thereof; to a patient in need of such treatment. For use in the instant method oral administration of a dose of from about 10 to 60 mg of an azapirone at the hour of sleep is usually employed.

DETAILED DESCRIPTION OF THE INVENTION

The invention results from the discovery that buspirone administration is an effective treatment in preventing or reducing the incidence of sleep apneas. In the context of this invention, sleep apneas comprise all the sub-categories such as those caused by upper airway obstruction; those whose origins arise in the central nervous system; and those of a mixed type with contribution from both components. This invention is also intended for use in "sudden infant death syndrome" (SIDS). It should be appreciated that no established therapy for sleep apneas exists. As an example, treatment modalities for the most common subtype, chronic obstructive sleep apnea, have included weight loss, surgical removal of tissue that may cause obstruction, avoidance of all sedatives, mechanical interventions and oxygen masks. None of these measures has been effective in any consistent manner. In this as well as other sleep apneas, pharmacologic intervention has been used but effectiveness has not been established. Respiratory stimulants, antidepressants, theophylline and various progestational agents have been tried but not found to be very effective.

A recent review (Guilleminault, "Obstructive Sleep Apnea Syndrome", in *Psychiatric Clinics of North America*—Vol. 10, No. 4, pages 607–618 (1987)) reveals a widespread occurrence as well as a range of serious medical sequelae.

Also in the context of this invention is the use of other azapirones in addition to buspirone, in treating sleep apnelas.

The method of the present invention then is intended to encompass the use of related azapirone compounds of Formula I.

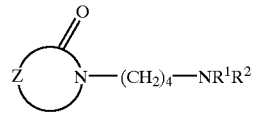

I

In Formula I, Z is a member selected from the group with $R^3$ and $R^4$ being independently selected from $C_{1-4}$ alkyl and hydrogen or $R^3$ and $R^4$ can be taken together as a butanediyl or pentanediyl chain thereby forming a spiro ring system. $R^1$ and $R^2$ in Formula I are either taken together as thereby forming a pyrimidinylpiperazine moiety, or $R^1$ is hydrogen and $R^2$ is the group A can be —$CH_2$—, —O—, —$CH_2CH_2$—or —CH=CH—. The dotted and solid line represents either a single or a double chemical bond.

Preferred azapirones are the following compounds, listed below in Table 1, which have been disclosed previously as psychotropic agents with useful anxiolytic properties.

TABLE 1

Specific Azapirone Compounds

| STRUCTURE | REFERENCVE |
|---|---|
| BUSPIRONE | U.S. Pat. No. 3,717,634 |
| GEPIRONE | U.S. Pat. No. 4,423,049 |

TABLE 1-continued

Specific Azapirone Compounds

| STRUCTURE | REFERENCVE |
|---|---|
| 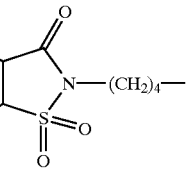 IPSAPIRONE | EP 129,128A |
| 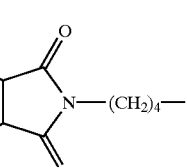 SM-3997 | U.S. Pat. No. 4,507,303 |
| 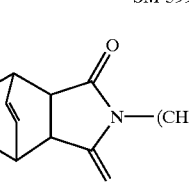 WY-47,846 | J. Med. Chem., 1988 1382–1392 |
| 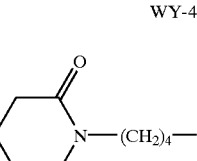 MOL 72832 | U.S. Pat. No. 4,612,312 |

There are two aspects to the use of azapirones in treating sleep apneas. The first is that the administration of an azapirone effectively reduces the frequency and severity of the apnea episodes during sleep. This is reflected in significantly increased undisturbed sleep and a significant increase in blood oxygen levels. The second aspect involves azapirone alleviation of the symptomatology associated with the occurrence of sleep apneas. The azapirone treatment alleviates the sleep apnea-related symptoms of anxiety, depression, fatigue, malaise, irritability, anger and hostility.

Clinical experience with selected azapirones would indicate that maximum response levels to azapirone administration may require a period of chronic administration, in some instances on the order of two to four weeks. It is appreciated by those skilled in the art that the time to emergence of full therapeutic response, as well as the dosage level required, can vary from patient to patient.

The effectiveness of azapirone treatment of patients suffering from sleep apneas can be exemplified by clinical experience with buspirone. Single dose administration of buspirone, given at bedtime to patients suffering from obstructive sleep apnea, resulted in increased sleep efficiency with experimentally derived measurements showing a gain in total sleep time and a marked reduction in episodes of sleep disturbance. One of the most consistent physiological measurements of improvement was a 10 to 20% increase in blood oxygen levels, an indication of improved respiratory efficiency.

In summary, the present invention concerns a method for treating sleep apneas comprising obstructive, central and mixed apneas, in a patient population that ranges from infants to geriatric-aged individuals. The method of treatment involves administration of buspirone, or another azapirone given as the azapirone base or one of its pharmaceutically acceptable salts, in the form of a pharmaceutical composition, either alone or as an adjunct to their therapies.

Pharmaceutically acceptable acid addition salts of buspirone and methods of pharmaceutical formulation are described in the patents of Wu, et al., U.S. Pat. No. 3,717,634 and U.S. Pat. No. 3,976,776, which are incorporated in their entirety herein by reference. Substitution of other azapirone agents may be made with slight variation in method or as set forth in the pertinent references given supra, which are herein incorporated by reference.

Administration of azapirone according to the present invention may be made by the parenteral, oral, or rectal routes. Parenteral administration comprises injection, e.g., intravenous or intramuscular injection, as well as any other parenteral route of administration. The oral route is preferred. The clinical dosage range for treatment of sleep apneas depend on age of recipient, body weight, general physical condition and severity of sleep apnea disorder. In general the drug treatment will be administered at the hour of sleep and will be about 20 to 40 mg for an average adult. Dosage will be appropriately reduced for infants and young children, according to the clinical judgment of the attending physician. Consistent with good clinical practice, some dose adjustments may be employed in the prescribing of the treatment for individual patients, and such dose adjustment is known to one skilled in the medical arts.

What is claimed is:

1. A method for treatment of sleep apneas comprising administration of a therapeutically effective amount of a Formula I azapirone compound or a pharmaceutically effective acid addition salt thereof to a patient in need of such treatment;

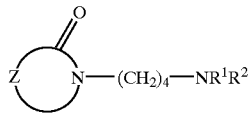

wherein

Z is a member selected from the group consisting of

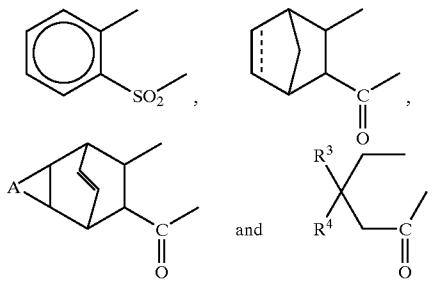

with the dotted and solid line representing either a single or a double chemical bond; A being selected from the group consisting of O, $CH_2$, $CH_2CH_2$ and CH=CH;

$R^3$ and $R^4$ being independently selected from hydrogen and $C_{1-4}$ alkyl or $R^3$ and $R^4$ can be taken together as a butanediyl or pentanediyl chain; and $R^1$ and $R^2$ are either taken together as

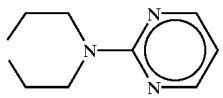

or $R^1$ is hydrogen and $R^2$ is

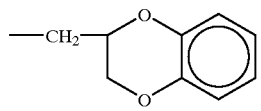

2. The method of claim 1 wherein Z in the Formula I compound is

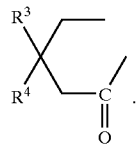

3. The method of claim 1 wherein Z of the Formula I compound is

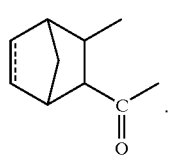

4. The method of claim 1 wherein Z of the Formula I compound is

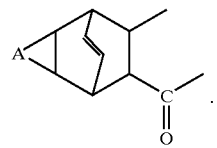

5. The method of claim 1 wherein Z of the Formula I compound is

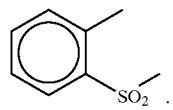

6. The method of claim 1 wherein $NR^1R^2$ is

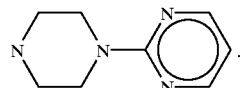

7. The method of claim 1 wherein the Formula I compound is buspirone.

8. The method of claim 1 wherein the Formula I compound is gepirone.

9. The method of claim 1 wherein the Formula I compound is ipsapirone.

10. The method of claim 1 wherein the Formula I compound is

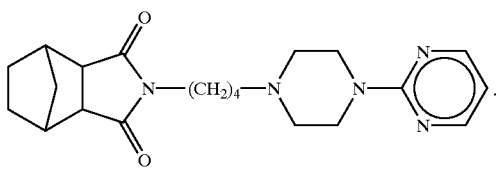

11. The method of claim 1 wherein the Formula I compound is

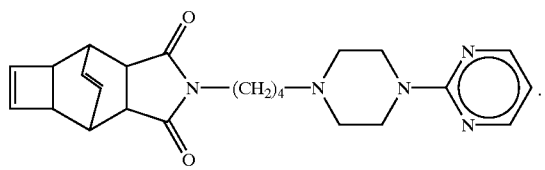

12. The method of claim 1 wherein the Formula I compound is

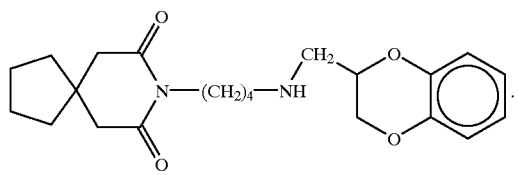

13. The method of claim 1 wherein buspirone hydrochloride is employed and dosage is by the oral route.

* * * * *